(12) United States Patent
Hodge et al.

(10) Patent No.: US 7,258,879 B1
(45) Date of Patent: Aug. 21, 2007

(54) FOOD PRODUCT AND PROCESS FOR MANUFACTURING SAME

(75) Inventors: Jason Hodge, Port Lonsdale (AU); Louise Richardson, Wodonga (AU); Neil Stoodley, deceased, late of Bradford (GB); by Keith Stoodley, legal representative, Bradford (GB); Catriona Julie Gifford, Leicestershire (GB); Stella Collins, Manchester (GB)

(73) Assignee: Mars, Inc., McLean, VA (US)

( * ) Notice: Subject to any disclaimer, the term of this patent is extended or adjusted under 35 U.S.C. 154(b) by 604 days.

(21) Appl. No.: 10/070,526

(22) PCT Filed: Sep. 6, 2000
(Under 37 CFR 1.47)

(86) PCT No.: PCT/AU00/01055

§ 371 (c)(1),
(2), (4) Date: Oct. 27, 2003

(87) PCT Pub. No.: WO01/17364

PCT Pub. Date: Mar. 15, 2001

(30) Foreign Application Priority Data

Sep. 6, 1999 (AU) .................................. PQ2665
Jan. 20, 2000 (AU) .................................. PQ5182

(51) Int. Cl.
*A23K 1/00* (2006.01)
*A23K 1/175* (2006.01)

(52) U.S. Cl. .............................. 426/2; 74/615; 74/655; 74/656; 74/658; 74/661; 74/805

(58) Field of Classification Search .................... 426/2, 426/656, 658, 72, 74, 661, 654, 648, 805, 426/615, 655
See application file for complete search history.

(56) References Cited

U.S. PATENT DOCUMENTS

| | | | |
|---|---|---|---|
| 4,046,922 A * | 9/1977 | Burkwall, Jr. .............. 426/104 |
| 4,267,195 A | 5/1981 | Boudreau et al. |
| 4,282,254 A | 8/1981 | Franzen et al. |
| 4,296,132 A | 10/1981 | Lazarus et al. |
| 4,451,488 A * | 5/1984 | Cook et al. .................... 426/89 |
| 4,804,549 A | 2/1989 | Howley et al. |
| 5,405,836 A * | 4/1995 | Richar et al. ................. 514/23 |
| 5,439,924 A * | 8/1995 | Miller ........................ 514/345 |
| 5,643,623 A | 7/1997 | Schmitz et al. |
| 5,786,382 A * | 7/1998 | Childers-Zadah .......... 424/733 |
| 5,922,692 A | 7/1999 | Marino |
| 6,050,224 A * | 4/2000 | Owens ........................ 119/710 |
| 6,156,355 A * | 12/2000 | Shields et al. ................ 426/74 |
| 6,165,474 A * | 12/2000 | Frudakis et al. ............. 424/737 |
| 6,228,418 B1 * | 5/2001 | Gluck et al. ................ 426/623 |
| 6,379,725 B1 * | 4/2002 | Wang et al. .................. 426/72 |
| 6,391,375 B1 * | 5/2002 | Fone ............................ 426/635 |

FOREIGN PATENT DOCUMENTS

| | | |
|---|---|---|
| EP | 0 862 863 | 10/2001 |
| JP | 07-222555 A | 8/1995 |
| JP | 07-241169 A | 9/1995 |
| JP | 3042830 | 8/1997 |
| JP | 10328284 | * 12/1998 |
| WO | WO97/29763 | 8/1997 |
| WO | WO-98/44932 | 10/1998 |
| WO | WO99/47000 | 9/1999 |

OTHER PUBLICATIONS

Abood, N. American Veterinary Conference Proceedings, vol. 12, May 1999, downloaded from http://www.thecapsulereport.com/sa18,1-3.htm.*

(Continued)

*Primary Examiner*—C. Sayala
(74) *Attorney, Agent, or Firm*—Fulbright & Jaworski; Jan K. Simpson (57) ABSTRACT

This invention is concerned with packaged food products which contain specific combinations of functional additives aimed at addressing specific health indicators, in particular flatulence, gastro-intestinal health, stress and immune system responsiveness, in pet animals. There is provided a commercially packaged mammal pet food product that includes a manufactured, shelf-life stable food substrate and a combination of functional additives. The functional additives include at least one non-palatable plant-based remedy and/or dietary fiber source that are present to strengthen and/or maintain a specified health indicator of a mammal pet animal. The food product is portioned and packaged with the functional additives being present in predetermined concentrations and amounts sufficient to be effective in achieving said indications on regular feeding of the pet animal with said food product. The food substrate is present in a proportion sufficient to mask the flavor and/or odor of the non-palatable additive and is made-up of a unique combination of materials that are able to be processed at lower temperatures to preserve the natural botanical functional additive's activity. Functional additives intended to address dietary flatulence problems include a combination of Yucca extract, charcoal and salts of zinc, such as zinc acetate. Functional additives to promote or maintain gastro-intestinal health include a combination of L-glutamine, D-glucosamine sulphate, sugar beet pulp, slippery elm. Functional additives to strengthen or maintain a pet animal's natural body defenses include a combination of vitamin E, vitamin B complex, primrose oil vitamin C and Marigold meal. Functional additives to promote or maintain reduction of stress and/or improved behavior of a pet animal include a combination of Valerian root extract, Kava root extract, vitamin B complex and magnesium salt.

17 Claims, 3 Drawing Sheets

OTHER PUBLICATIONS

Suarez F.L., Springfield J, & Levitt MD (1998) "Identification of gases responsible for the odour of human flatus and evaluation of a device purported to reduce this odour". Gut. 43.100-104.*

Lowe JA, Taylor AJ and Linforth R (1997) 'q-he effect of Yucca Shidigera extract on canine and feline faecal volatiles occurring concurrently with faecal aroma amelioration, Research in Veterinary Science 63, pp. 67-71.*

Jain et al., Annals of Internal Medicine, vol. 105, No. 1, pp. 61-62, Jul. 1986.*

M.D. Willard, et al.; *Effects of Dietary Supplementation of Fructo-Oligosaccharides on Small Intestinal Bacterial Overgrowth in Dogs*; American Journal of Veterinary Research, vol. 55, No. 5, May 1994.

* cited by examiner

Fig. 1

Human Perception Rating= 1.511124 * Sulfur Gas (ppm) ^ 0.280379

FOOD PRODUCT AND PROCESS FOR MANUFACTURING SAME

FIELD OF THE INVENTION

This invention relates to packaged food products for regular feeding of mammal pet animals and which contain functional additives to enhance specific health aspects of the pet animal. The invention also relates to a process for manufacturing a palatable pet food product containing such functional additives.

In a further aspect, the invention is concerned with packaged food products which contain specific combinations of functional additives aimed at addressing specific health indicators, in particular flatulence, in pet animals.

BACKGROUND OF THE INVENTION

In the manufacture of packaged pet food products, in particular dried and canned pet food for dogs and cats, it is known to add nutritional supplements, such as vitamins, minerals and the like to satisfy basic dietary requirements of the animal.

In the case of most vitamin and mineral supplements, the amounts mixed into the food product to achieve general health benefits are small enough to not adversely affect the palatability of the overall product. In essence, the food product will be eaten by the pet animal regardless of the presence or absence of such additives.

On the other hand, inclusion in the pet food product of dietary fibre source material in amounts sufficient to achieve a "balanced" diet will often lead to packaged products that are not readily accepted by the pet animal, due to its reduced palatability.

Like other creatures, dogs, cats and other companion animals suffer various ailments and health conditions that often require appropriate forms of medication and/or other treatment. It is well known that medications and remedies for companion animals can be provided in the form of tablets, powders or liquids for oral administration. However, many pet animals are reluctant to take such tablets, powders or liquids and having to force these into the animal's mouth can be stressful for both the animal and the person administering the medication.

For these reasons, especially if the medication or remedy is unpleasant tasting, pet owners often mix the medication/remedy with the animal's normal daily food, so as to hopefully mask the unpleasant taste. This procedure is inconvenient, cumbersome and sometimes subject to "trial and error", as the "masking" effect is not necessarily always achieved and the medication or remedy infused food may end up being rejected by the animal.

It is also known in the pet care industry to incorporate pharmaceutical medications into an edible food substrate, primarily for the purpose of masking the taste of the medication and/or improving administration to the animal. Typically, the pharmaceutical medication is mixed during manufacture of the end product with a pleasant tasting substance (e.g. meat analogue product) and subsequently packaged into individually administrable portions which can then be bought at supermarkets, veterinary surgeries and the like. Examples of such type of product which incorporate synthetic pharmaceutical drugs are Exelpett™, Ezydose Allwormer and Heartguard™. These products are essentially pharmaceutical products that are administered in addition to the animal's usual daily meals, such that when the course of treatment is over and the pet animal's health concerns have been rectified, administration of the relevant product can be easily discontinued. Accordingly, such products are generally only used spasmodically as a short-term treatment regime for pet animal diseases.

With the increasing use of "alternative" disease treatment regimes in humans, it has also become known that plant-based remedies that are beneficial in ameliorating various human ailments, can be equally used to treat or ameliorate ailments in pet animals. Plant-based remedies include different types of essential oils, herbal extracts, powdered herbs, roots, leaves and tree barks, comestible plant fibre etc. Hereinafter this group of ingredients are simply referred to by the colloquial expression "herbal medicines or remedies".

Herbal medicines have been devised by individual pet owners to address specific, mainly diet-based ailments of dogs and cats. Herbal medicines can be administered orally directly into the mouth of the pet animal, or by admixing it with the pet animal's daily meal. However, many herbal remedies are indeed far more unpleasant to taste and/or smell than pharmaceutical drugs. Although this unpleasant taste is generally not a major concern with humans, who can be persuaded to bear the unpleasant taste on the basis that they will benefit from taking the herbal remedy, the situation with pet animals is very different. Their sense of smell and taste will often make the task of "masking" the unpleasant tasting herbal remedy with other food additives and/or food ingredients far more complicated than is the case with the pharmaceutical drugs. This in turn makes the task of finding a suitable carrier for administration of herbal remedies to pet animals difficult to achieve on a commercial food manufacturing scale. Some problems that need to be addressed are shelf-life, degradation of the herbal remedy when in contact with other food substances over prolonged storage periods, stability of the product, basic binding to preserve activity of herbal ingredients, amongst others.

One of the more common diet-related problems among companion animals is flatulence and their gastro-intestinal health (GIH). The unpleasant odour associated with flatulence constitutes a significant psycho-sociological problem in animal-owner relationship, let alone the possible underlying gut health aspects. Human studies have demonstrated the detrimental effects of toxic sulphur compounds present within intestinal gas on the health of the large intestine, and such compounds have been implicated in the pathogenesis of ulcerative colitis. The major components of intestinal gas which lead to flatulence are odourless gases, including nitrogen, hydrogen, carbon dioxide, methane and oxygen. However, trace quantities of toxic sulphurous gases, such as hydrogen sulphide are responsible for flatus odour. Sulphate reducing bacteria (SRB) are the bacterial genus responsible for reducing sulphate to sulphide, thereby generating hydrogen sulphide. Research in the human field has focussed on the determination of gas volumes which lead to bloating and discomfort, whilst in the animal field research has centred on the characterisation of offensive odours within flatus.

Several prior art documents disclose remedies to reduce the flatulence and/or the offensive odour associated therewith. For example, U.S. Pat. Nos. 5,716,641 and 5,679,376 disclose certain pharmaceutical compositions that are reported to reduce flatulence. Some of these compositions are based on simethicone.

The removal from food of materials believed to be strongly implicated in the production of flatulence (such as certain sugars and oligosaccharides) has also been described. For examples, see U.S. Pat. Nos. 5,871,801 and 4,645,677.

The use of dietary supplements and additives to reduce flatulence odour is less well reported in the patent literature. There are a few examples, such as the addition of chitosan (e.g. see U.S. Pat. No. 5,773,427) or fumaric acid (e.g. see U.S. Pat. No. 5,589,186) to the diet.

Salts of zinc are known to react with volatile sulphur gases, especially $H_2S$ (e.g. see U.S. Pat. No. 5,405,836). The use of dietary zinc salts to reduce the $H_2S$ content of intestinal gases has also been suggested in the published literature, e.g. see Suarez F. L., Springfield J, & Levitt M D (1998) "Identification of gases responsible for the odour of human flatus and evaluation of a device purported to reduce this odour". Gut. 43.100-104.

The inclusion in the diet of extracts of Yucca Shidigera (or Yucca Elata) has been shown to reduce the malodour of canine and feline faeces (e.g. see Lowe J A, Taylor A J and Linforth R (1997) "The effect of Yucca Shidigera extract on canine and feline faecal volatiles occurring concurrently with faecal aroma amelioration", Research In Veterinary Science 63, pages 67-71, from which it is reasonable to infer that flatulence malodour would also be reduced.

Charcoal is also known as an adsorbent for noxious gases, and its ability to reduce flatus malodour within a cushion has been proven (again see article by Suarez et al). Charcoal is also a component in a small number of orally administered odour-reducing products currently on the market.

Because of physiological similarities, one can assume that substances and mixtures of compounds that successfully address flatulence problems perceived to exist in dogs and cats, could be adapted for consumption by humans.

The present invention has been devised in light of perceived problems associated with the administration of per se non-palatable dietary health supplements to pet animals.

One aim of the invention is to provide a commercially packaged pet food product for administration to a mammal pet animal on a regular basis, i.e. in the form of "treat" products, in accordance with a recommended feeding regime, in addition to the regular daily diet of the animal, that will contribute in maintaining and/or improving specific health indicators of the pet animal.

Within this broader aim, it would be advantageous to provide a packaged pet food product that when taken on a regular, e.g. daily basis, ameliorates flatulence related odour problems with a pet animal.

Also within the broader aim, it would be advantageous to provide a packaged pet food product which will improve overall gastro-intestinal health of the pet animal when consumed on a regular, ongoing basis.

Within the above stated broader aim, it would be similarly advantageous to provide a packaged pet food product which, taken on a regular daily basis, is capable of strengthening the immune system of the pet animal.

Also within the broader aim, it would be advantageous to provide a packaged pet food product which when taken on a daily basis will alleviate "stress" related conditions of the pet animal.

Within the scope of the above aims it is intended to provide palatable pet food product recipes that incorporate plant-based dietary functional additives and combinations thereof that achieve the improvements in relation to the health indicators mentioned above, and which can be packaged as a "treat" product.

The term packaged pet food product is used herein to generally encompass dried food pellets, biscuits, bars, "chewy bites" and similar products that are given by a pet owner to a cat or dog as a "treat", e.g. once a day, in addition to the normal diet.

DETAILED DESCRIPTION OF THE DRAWINGS

SUMMARY OF THE INVENTION

The invention concerns a commercially packaged mammal pet food product that includes a manufactured, shelf-life stable food substrate and a combination of functional additives. The functional additives include at least one non-palatable plant-based remedy and/or dietary fibre source that are present to strengthen and/or maintain a specified health indicator of a mammal pet animal, wherein the food product is portioned and packaged with the functional additives being present in predetermined concentrations and amounts sufficient to be effective in achieving said indications on regular feeding of the pet animal with said food product, and wherein said food substrate is present in a proportion sufficient to mask the flavour and/or odour of the non-palatable additive.

Depending on the specific functional additives that are present, the composition of the food substrate may vary, as is explained below in greater detail.

An acceptable palatability measure is given where no more than 10%, but preferably 5%, of the product is refused when offered to the animal over a 7 day period on a regular and/or exclusive basis.

In addition to the relevant functional additives, other active dietary supplements known to have, individually, specific health-improving properties, such as vitamins, mineral supplements and the like, may be incorporated into the packaged product. In order to achieve and maintain a specific health indication in accordance with the invention, additional functional additives in the form of plant materials that provide a source of natural dietary fibre and/or herbal remedies that exhibit a medicinal and/or therapeutic benefit are incorporated in specified quantities/amounts into the pet food product during its manufacture.

DETAILED DESCRIPTION OF INVENTION

Accordingly, in a first aspect of the invention, the functional additives of the pet food product are intended to address dietary flatulence problems and will include a combination of Yucca extract (eg Yucca Shidigera or Elata), charcoal and salts of zinc, such as zinc acetate, said functional additives being provided in amounts sufficient to reduce flatulence odour when the pet food product is provided to a pet animal on a daily basis. It has been observed that the use of any two of these functional additives in combination results in reduction of flatulence odour, with the specific combinations of zinc acetate and charcoal or zinc acetate, charcoal and Yucca extract showing certain synergistic effects. Preferably, these functional additives are provided in the following amounts, the balance being made up by the food substrate and other normal nutritional supplements:

Yucca Shidigera or Elata extract—from about 0.04 to about 0.11% by weight of finished product, preferably 0.05%;

Vegetable charcoal—from about 5 to about 14% by weight of finished product, preferably 6%;

zinc acetate—from about 0.3 to about 0.8% by weight of finished product, preferably 0.32%.

The recommended daily ingestion of these, combined functional additives to achieve the desired flatulence reducing health benefits will generally be within the following range of finished product mass:

| Animal Mass | Daily Dosage |
|---|---|
| <7 kg | 2.5 g |
| 7-14 kg | 5.0 g |
| 15-25 kg | 10 g |
| >25 kg | 20 g |

In a second aspect of the invention, the functional additives will include a combination of L-glutamine, D-glucosamine sulphate, sugar beet pulp, slippery elm (Ulmus Fulva) and optionally inulin, said functional additives being provided in amounts sufficient to promote or maintain gastro-intestinal health when the pet food product is provided to the pet animal on a daily basis.

These functional additives are preferably provided in the following amounts, the balance being made up by the food substrate and other normal nutritional supplements:

L-glutamine—from about 3 to about 5% by weight of finished product;

D-glucosamine sulphate—from about 3 to about 5% by weight of finished product;

sugar beet pulp—from about 4 to about 8% by weight of finished product;

a if present inulin—from about 3.0 to about 4.5% by weight of finished product; and slippery elm—from about 1.5 to about 2.5% by weight of finished product.

It is particularly preferred that the above functional additives are provided in the following amounts:

L-glutamine—about 4% by weight of finished product;

D-glucosamine sulphate—about 4% by weight of finished product;

sugar beet pulp—about 6% by weight of finished product;

inulin—about 3.9% by weight of finished product; and slippery elm—about 2% by weight of finished product.

The recommended daily ingestion of these, combined functional additives to achieve the desired gastrointestinal health benefit will generally be within the following range of finished product mass:

| Animal Mass | Daily Dosage |
|---|---|
| <7 kg | 2.5 g |
| 7-14 kg | 5.0 g |
| 15-25 kg | 10 g |
| >25 kg | 20 g |

In a third aspect of the invention, the functional additives include a combination of vitamin E, vitamin B complex, primrose oil (e.g. Oenothera Biennis), vitamin C and Marigold meal (e.g. *Calendula Officinalis*). The functional additives are provided in amounts sufficient to strengthen or maintain a pet animal's natural body defenses (immune system function) when the pet food product is provided to the pet animal on a daily basis. These functional additives are preferably provided in the following amounts, the balance being made up by the food substrate and other normal nutritional supplements:

vitamin E—about 1.0 to about 2.5% by weight of finished product, preferably about 2%;

vitamin B complex—about 0.10 to about 0.25% by weight of finished product, preferably 0.2%;

evening primrose oil—about 0.7 to about 2.5% by weight of finished product, depending on the essential oil content, preferably about 0.8%;

vitamin C—about 0.5 to about 3% by weight of finished product, preferably about 2.5%;

marigold meal—about 0.4 to about 0.8% by weight of finished product, preferably about 0.6%.

The recommended daily ingestion of these, combined functional additives to achieve the desired immune system benefits will generally be within the following range of finished product mass:

| Animal Mass | Daily Dosage |
|---|---|
| <7 kg | 2.5 g |
| 7-14 kg | 5.0 g |
| 15-25 kg | 10 g |
| >25 kg | 20 g |

In a fourth aspect of the invention, the functional additives will include a combination of Valerian root extract (e.g. Valerian Officinalis), Kava root extract (Piper Methysticum), vitamin B complex and magnesium (in a digestible salt form). The functional additives being provided in amounts sufficient to promote or maintain reduction of stress and/or improved behavior of a pet animal when the pet food product is provided to the pet animal on a daily basis. In addition to or in partial substitution for Valerian root extract and/or Kava root extract, Gingko Bilboa extract and St John's Wort extract (Hypericum Perforatum) may be added in a physiological relevant amount to develop their known nerve calming properties.

It is preferred that the functional additives are provided in the following amounts, the balance being made up by the food substrate and other normal nutritional supplements:

Valerian root extract—from about 0.3 to about 1% by weight of finished product;

if present, Gingko Bilboa extract—from about 0.1 to about 1.3% by weight of finished product;

if present, St John's Wort extract—from about 0.1 to about 1.3% by weight of finished product;

Kava root extract—from about 0.3% to about 3.0% by weight of the finished product;

vitamin B complex—from about 0.5 to about 3.0% by weight of finished product;

magnesium salt—from about 0.5 to about 2.5% by weight of finished product.

In particular, it is preferred that the above functional additives are provided in the following amounts:

Valerian root extract—about 0.4% by weight of finished product (depending on the concentration of the pure essence);

Kava root extract—about 2% by weight of the finished product;
vitamin B complex—about 2.5% by weight of finished product;
magnesium sulphate—about 1.8% by weight of finished product.

The recommended daily ingestion of these, combined functional additives to achieve the stress reduction health benefit will generally be within the following range of finished product mass:

| Animal Mass | Daily Dosage |
|---|---|
| <7 kg | 2.5 g |
| 7-14 kg | 5.0 g |
| 15-25 kg | 10 g |
| >25 kg | 20 g |

The manufactured food substrate will generally include a recipe of dry ingredients and at least one liquid ingredient, which whilst commonly used in the pet food manufacturing industry have to be formulated with the taste masking capability of individual constituents in mind, as well as to maintain the functionality of the additives. The water content of the finished product will largely depend on whether the product is a "dry", biscuit-style treat or a "meaty chew" bar or bite food product.

In accordance with the invention there is provided a unique combination of materials that make up the food substrate, in that the materials are able to be properly processed at lower temperatures to preserve the natural botanical functional additive's activity. Sugar-based compounds (e.g. combinations of sugar and/or glucose, and/or dextrose, and/or maltodextrines) provide preservation and textural variation.

Compounds that are suited to adequately mask unpalatable (odour and/or taste) functional additives include dry food substrate ingredients based on animal proteins and carbohydrates. To these is generally added an anti-microbial agent. The animal protein will generally constitute from about 17% to 50% by weight of the dry ingredients and serve as the main flavouring agent of the food product to mask the functional additives, whereby the animal protein will usually be derived from beef, pork, mutton, poultry, fish or a combination of these. The animal protein preferably includes gelatins as binding agents. The carbohydrates generally include simple and complex carbohydrates, the latter typically consisting of or including rice flour, the former generally consisting of or including glucose, glycerol and/or sugar. The antimicrobial agent is preferably potassium sorbate. The at least one liquid ingredient of the pet food product is preferably water and an antioxidant, which preferably is rosemary extract.

The water may constitute in a finished biscuit-style product less than 5% by weight, and from as little as about 10 to about 20% by weight where the finished food product is a palatable, 'treat'-sized, chewy tablet. The latter has a base consisting mainly of cooked, pulverized animal meats and bones which have been compression-moulded into a portion-shape.

A palatable pet food product in the form of a palatable, 'treat'-sized, chewy tablet, may typically include ingredients in the following proportions by weight of finished product:
gelatine—from about 3 to about 7%;
glucose—from about 2 to about 5%;
sugar—from about 2 to about 5%;
glycerol—from about 1 to about 4%;
potassium sorbate—from about 0.2 to about 0.5%;
rosemary extract—from about 0.01 to about 0.05%,
water—from about 10 to about 20%; and
the balance being composed of pulverised meat (approx 50%), cereal flour (approx 11%), sugar (approx 8%), glycerine (approx 9%), citric acid (approx 1%) and preservatives (approx 0.1%).

The pet food product described above may be provided in any suitable shape, so as to facilitate administration to a pet animal of a desired amount of the product corresponding with a desired dosage. Accordingly, the pet food product may be provided in the form of single biscuits, in which case each biscuit contains a substantially identical, predetermined dosage of the functional additives. Alternatively, the pet food product may be provided as a food bar, in which case the food bar has substantially uniform concentration of the at least one functional additive throughout the length of the bar. The food bar may then include markings, etchings or the like for indicating where the bar may be broken so as to provide the pet animal with the desired dosage of the functional additives.

In a manufacturing process aspect of the invention there is provided a process for manufacturing a palatable, treat-style pet food product using dry and liquid ingredients and functional additives, of the type described above, including the steps of:
mixing the dry ingredients which include animal protein, carbohydrates and an antimicrobial agent;
heating the dry ingredient mixture to between 50 to 80° C., preferably about 60° C., for about 5 to 15 minutes, preferably about 10 minutes;
adding the functional additives to the dry ingredient mixture;
mixing the resultant mixture for about 5 minutes;
heating, in a separate container, liquid ingredients, including water and an antioxidant, to between 60 to 85° C., preferably about 75° C.; adding the heated liquid ingredients to the resultant mixture to obtain a moistened mixture;
heating the moistened mixture to between 60 to 80° C., preferably about 75° C., for about 5 minutes to obtain a cooked mixture;
substantially immediately after the heating step subjecting the cooked mixture to a cooling step to achieve a processed mixture temperature of between 40 to 60° C., preferably about 50° C.; and
moulding the cooled processed mixture by impression moulding or cutting techniques so as to form a packagable product of predetermined treat size, shape and weight.

In case of a divisible pet food product, the process may further include the step of making markings, etchings or the like on the moulded product so as to enable the packaged product, in use, to be easily broken into pieces of a particular size.

It has also been discovered that the above referenced combination of Yucca Shidigera extract, vegetable charcoal and zinc acetate, when mixed into a carrier suitable for human consumption, will also have positive effects with regards to flatulence problems perceived by humans. One way of ensuring easy administrability of these functional additives to e.g. children is to mix these constituents into a conventional short biscuit recipe. The short biscuit recipe may includes, in weight-% of non-water or milk components, 31% butter or shortening, 17% icing sugar, 39% biscuit flour, vegetable charcoal from about 10 to 12%, Yucca extract from about 0.07 to 0.12% and zinc acetate from about 0.5 to 0.8%, bearing in mind that the RDA of zinc is about 15 mg in accordance with the European Union Nutrition labelling Directive.

Other aspects of the invention will become apparent from the following description of tests carried out to show the health-benefits that are obtainable by pet animals when fed with different food recipes containing different combinations of functional additives.

1. Pet Food Products Aiming to Reduce Flatulence

The following examples are directed to the aspect of the invention directed to reducing flatulence odour in pet animals by daily feeding of a supplementary treat, in conjunction with its normal feeding regime.

In order to demonstrate the benefits of the formulations of this aspect of the invention, two methods were used. The in vitro method is described in detail below under the heading, "In Vitro Method". The novel in-vivo method is described below under the heading "In Vivo Method".

a) In Vitro Method

This Method has Been Used to Measure In Vitro Hydrogen Sulphide.

Sample Preparation

Active ingredient concentrations were chosen to correspond to those levels that would be incorporated into a pet food product treat. Ingredients were weighed into triplicate glass serum bottles containing 30 mL of fermentation media; bottles were capped with a cotton wool bung and covered with foil. Bottles were prepared with no active ingredient to act as controls. 200 mL of 10 mM sodium phosphate buffer, pH 7.4 was prepared in conical flasks, containing a flea, for faecal resuspension. Bottles were sterilised by autoclaving (15 min, 121° C.) and placed into the anaerobic cabinet to attain anaerobic conditions (pre-reduction).

Faecal Inoculation

Fresh faecal samples were collected, scored and weighed. A sample of faeces was freeze-dried to determine faecal dry weight. 20 g of faeces were added to the pre-reduced phosphate buffer within 15 min of defecation. The flask was placed on a magnetic stirrer (10 min) in the anaerobic cabinet to generate a faecal slurry. Cotton wool bungs were removed and 3 ml aliquots of faecal slurry were added to each serum bottle containing active ingredients and control bottles with no added active ingredient. This results in a 1% faecal inoculum per bottle. Bottles were hermetically sealed with rubber bungs and metal caps.

Bottles were inoculated in triplicate. Three bottles with no active ingredient were used as media and faeces controls. Three bottles with no active ingredient contained 1 ml of 10% molybdate, to inhibit sulphate reducing bacteria. All bottles were left to incubate for 24 hrs at 37° C.

The potential effects of the 3 active ingredients have been measured in terms of the total gas produced, and the level of hydrogen sulphide present in the in vitro fermentation broths.

Hydrogen Sulphide

To determine hydrogen sulphide, the following procedure was followed.

(i) A 1:4 dilution of broth in deoxygenated water was prepared.

(ii) The sample was spun at 13,800 g for 15 minutes at room temperature.

(iii) Aliquots of the test sample were taken—in order to provide test samples and faeces blanks, all stored on ice until analysis.

Standard Curve

In order to identify the levels of hydrogen sulphide in a solution a standard curve within the range of 0-50 ppm of) sodium sulphide must be constructed for each set of samples analysed.

Sample Analysis

To each standard, using Camlab Sulphide reagents:
a. 1 ml of sulphide-1-reagent was added with mixing.
b. 1 ml of sulphide-2-reagent was added with mixing.
C. The absorbance was measured in a spectrophotometer at 670 nm.

Analysis of Test Samples 1. 2 mL of deoxygenated water were added to the faeces blanks and the absorbance at 670 nm measured.
2. Steps a-c above were repeated on the triplicate test samples in order to determine their sulphide concentration. Test samples were diluted as necessary in order to place them in the range of the standard solutions.

b) In Vivo Method

This in vivo method has been used to measure in vivo flatulence production.

The novel in vivo flatulence system employed in this study consists of a pump, which is fitted into a coat worn by the dog, which draws air from around the anal region. A plastic O ring containing holes 1 cm apart is placed around the tail and is positioned close to the anus. This is connected via a plastic tube to the pump. The pump has a sensor that detects sulphur gas.

The pumps were set to measure sulphur gas levels every 20 seconds so that a measure of sulphur gas produced by the dog over time was obtained.

Consumer perception analysis has been carried out to identify the human detection limits of individual flatulence episodes recorded with the in vivo sulphur gas pump. Simple regression analysis was carried out to identify correlations between perceived and measurable flatulence parameters. A strong correlation ($r=0.9224$) was identified between the human flatulence rating over a scale of 1-5 and in vivo sulphur gas levels. An equation was generated that enables identification of the human detection levels of subsequent in vivo sulphur gas measures.

The equation generated from consumer perception analysis was applied to sulphur gas readings obtained from the current trial and the human detection ratings of the recorded flatulence episodes were identified. An "episode" is any given period during which the sulphur gas reading is consistently greater than 1 ppm. Sulphur gas levels of and below 1 ppm were not detectable by the human odour judges.

In Vitro Experiment 1

An in-vitro fermentation system was set up in order to assess the active ingredients for their potential to reduce hydrogen sulphide and total gas production. Ingredients were weighed into glass serum bottles containing fermentation media. Some bottles were also prepared without active ingredients in order to act as controls. Bottles were sterilised and placed into an anaerobic cabinet. Samples of faeces were collected, slurried, and aliquots of this slurry added to the control bottles and the bottles containing active ingredients—the bottles were then sealed and incubated for 24 hours at 37 C.

Hydrogen sulphide concentration was determined by the assay as set out.

Table 1a shows the mean hydrogen sulphide levels that were present in fermentation broths following incubation with active ingredients. There were significant reductions in hydrogen sulphide with the individual active ingredients ($p<0.05$). Surprisingly, a synergistic effect of adding all 3 active ingredients was observed.

TABLE 1a

Mean hydrogen sulphide (ppm) following treatment with active ingredients

| Treatment | Hydrogen Sulphide (ppm)/(g) Wet Faeces (n = 3) | |
| --- | --- | --- |
|  | Mean | SE |
| Media and Faeces Control | 425.66 | 40.39 |
| Yucca Shidigera | 263.45 | 32.72 |
| Zinc Acetate | 158.03 | 25.47 |
| Charcoal | 128.91 | 14.87 |
| All 3 Actives | 58.06 | 0.92 |

In vitro Experiment 2

The experiment described above was repeated using binary mixtures of the actives.

Table 1b shows the mean hydrogen sulphide levels that were present in fermentation broths following incubation. The hydrogen sulphide levels for the control and the combination of all 3 actives are broadly similar to those determined in the previous example. The effect of the charcoal and zinc acetate appears, surprisingly, to be synergistic.

TABLE 1b

Mean hydrogen sulphide (ppm) following treatment with active ingredients

| Treatment | Hydrogen Sulphide (ppm)/(g) Wet Weight Faeces (n = 3) | |
| --- | --- | --- |
|  | Mean | SE |
| Media and Faeces Control | 398 | 19.86 |
| 3 Actives | 90.9 | 6.78 |
| Charcoal and Yucca | 174.63 | 44.07 |
| Charcoal and Zinc | 80.27 | 4.14 |
| Zinc and Yucca | 209.36 | 2.65 |

In-Vivo Experiment

Details of the novel in-vivo method are given above under the heading "In-vivo Method". In these experiments a treat containing all 3 active ingredients was compared with a control containing no actives, as shown in the recipes below.

| Ingredient | % Inclusion | |
| --- | --- | --- |
|  | Active | Control |
| Poultry powders | 15 | 15 |
| Beef Tallow | 6.5 | 6.5 |
| Salt | 1.8 | 1.8 |
| Potassium Sorbate | 0.2 | 0.2 |
| Antioxidant | 0.25 | 0.25 |
| Water | 9 | 9 |
| Sugars | 8 | 8 |
| Glycol | 2.3 | 2.3 |
| Glycerol | 9 | 9 |
| Flours | 41 | 41 |
| Flavour | 0.2 | 0.2 |
| Soya oil | 0.7 | 0.8 |
| Yucca Extract | 0.05 | 0 |
| Zinc Acetate | 0.32 | 0 |
| Charcoal | 5.97 | 0 |
| Pregelatinised Wheat Starch | 0 | 6 |

Sulphur gas measures were collected for each dog in duplicate from active and control trial phases. These were converted into a consumer detection level using the rating equation set out above. The numbers of flatulence events in each of the rating classes were determined as a percentage of the total events in each measurement period, compare perception rating graph, above. The reduction in the percentage of bad and unbearable episodes between active and control treats was highly significant ($p<0.05$). The figure below illustrates the mean percentage of combined bad and unbearable episodes produced when dogs were fed active and control treats.

In summary, the inclusion of the combined active or functional additives in a pet food product having a food substrate recipe of the kind that provides a palatable, "treat"-sized chewy pellet, in accordance with a daily dosage regime that is specific to the pet animal's weight, will tend to reduce flatulence related bad odours stemming from the animal's normal diet. The palatability of the treat was not adversely affected by inclusion of the active ingredients, as compared with the standard.

2. Pet Food Products with Improved Gastro-Intestinal Tract (GIT) Health Functionality.

The following example is directed to the aspect of aiming at improving GIT health in pet animals, specifically by improving the firmness of the stools passed by a canine pet animals.

a. Summary

In order to demonstrate the benefits of part of the formulation of this aspect, and thereby to determine suitable levels of functional ingredients to incorporate in a treat product to be fed on a daily basis, a feeding trial was carried out on a number of dogs. The trial involved adding Sugar Beet Pulp (SBP) at 6 levels (range 0% to 4.1%) and slippery elm meal at an average level of about 1.5% to 2.5% weight of total product weight to a dog treat, which was fed on a daily basis. Palatability was assessed and digestibility trials performed with all products.

The success of each product in improving GIT health was measured by a determination of faeces quality. Stools were examined and rated against criteria based on the 'firmness', or otherwise, of the stools. Those showing a 'loose', or diarrhea-like, texture were rated 'unacceptable'. Stools which were 'firm', able to be picked up whole, were rated 'ideal'.

At all levels of SBP inclusion a significantly improved faeces quality compared to the standard (0% inclusion) was observed. Wet faeces output increased as the SBP inclusion level increased. The apparent digestibility of the major nutrients tested showed a pattern of decreasing apparent digestibility as the level of SBP increased. However the decrease was not significant at all inclusion levels. The palatability of the final product was not adversely affected by SBP nor slippery elm meal inclusion as compared with the standard.

b. Background Information.

Sugar Beet Pulp (SBP) was chosen for this trial as a source of natural dietary fibre, due to its unusual analytical profile—SBP has a high ratio of soluble to insoluble fibre compared to other fibre sources. Also, whilst SBP has previously been used in dry dog food recipes to improve faeces quality, it was unknown whether its inclusion in, wet food formulations would adversely affect the palatability of the product. Slippery elm meal was thought to have by itself some health benefits, though in combination with other additives no reports are available. Literature reports and analytical data reveal that slippery elm is a good source of soluble fibres and mucopolysaccharides that would have a positive and complementary action with the SBP fibres in the bowl.

In the development of the formulation, a level of fibre inclusion equivalent to approximately 5 gm per 400 kcals of animal food intake has been found to be optimal. Increasing the fibre content above this gave unacceptably loose faeces output.

Full digestibility trials were performed with all products, using 6 dogs fed according to a 6×6 Latin Square design.

c. Method.

SBP was added at six levels (range from 0 to 4.1% weight in the recipe) to a standard canned product to achieve total dietary fibre levels in products ranging from 0.5% to 3.2% as is (measured by the Englyst procedure), which gave between 2.2 and 12.3 gm per 400 kcals PME.

The SBP was added to the background meat in the two lower levels of addition, and to both the background meat and the formed meat chunks to achieve the three higher levels of fibre addition. The control product had no SBP addition. (see table 1).

TABLE 1

Product specifications.

| Trial Number and Product Code | % SBP Inclusion in Background Meat | % SBP Inclusion In Formed Meat Chunks | Total % SBP Inclusion | Total Fibre Content of Product As Is (Englyst) | Fibre Content gm per 400 kcals PME |
|---|---|---|---|---|---|
| DT1245 A | 0 | 0 | 0 (control) | 0.5 | 2.2 |
| DT1246 B | 0.8 | 0 | 0.8 | 0.8 | 3.6 |
| DT1247 C | 1.7 | 0 | 1.7 | 1.2 | 5.3 |
| DT1248 D | 1.7 | 0.8 | 2.5 | 1.6 | 6.8 |
| DT1249 E | 2.5 | 0.8 | 3.3 | 2.5 | 10 |
| D1250 F | 3.3 | 0.8 | 4.1 | 3.2 | 12.3 |

The study involved 6 standard digestibility trial protocols, with the products allocated to the test dogs according to a 6×6 Complete Latin Square design. (table 2).

TABLE 2

Randomised Latin Square design used for order of feeding.

| Dog No | Order of Feeding of each Product to Each Dog | | | | | |
|---|---|---|---|---|---|---|
| B63 | E | A | F | B | C | D |
| B72 | A | D | B | C | E | F |
| B104 | C | E | A | F | D | B |
| B56 | B | F | D | E | A | C |
| B92 | D | B | C | A | F | E |
| B27 | F | C | E | D | B | A |

The dogs were fed at the correct level to maintain body weight. The amount each dog was offered is shown below in table 3.

TABLE 3

Food amounts offered to the dogs.

| Dog Number | B63 | B72 | B104 | B56 | B92 | B27 | Mean |
|---|---|---|---|---|---|---|---|
| Amount offered - all diets (gm) | 900 | 900 | 850 | 900 | 950 | 900 | 900 |

The dogs were fed for seven days on each diet. Before the start of each new diet the dogs were fed the control product for 2 days.

Faeces were collected from each dog during the last 4 days of each feeding period, freeze dried and analysed for proximate nutrients, collagen and gross energy.

The diets were analysed for proximate nutrients, vitamins, minerals, collagen, starch, dietary fibre and gross energy.

Faeces quality was measured subjectively on a linear scale and analysis of variance was conducted.

Dogs were weighed at the beginning and end of each feeding period and digestible energy intakes were related to body weight changes.

c. Results

Palatability (Acceptance) and Weight Changes

TABLE 4

Summary of intakes and weight changes.

| Diet | Total % SBP Inclusion | Acceptance | DE Intake kcals/day/Wt 0.75 | Weight Change (%) |
|---|---|---|---|---|
| DT1245 A | 0 (Std Product) | 100% | 105.7 to 139.01 | −3.0 to 0 |
| DT1246 B | 0.8 | 100% | 98.91 to 127.81 | −2.4 to 0 |
| DT1247 C | 1.7 | 100% | 95.88 to 130.66 | −0.8 to +0.7 |
| DT1248 D | 2.5 | 100% | 103.28 to 127.2 | −2.8 to +0.7 |
| DT1249 E | 3.3 | 100% | 107.69 to 130.69 | −2.9 to +2.1 |
| DT1250 F | 4.1 | 100% | 96.3 to 129.8 | −2.2 to +0.7 |

All weight changes were within the normal variation expected. Palatability was unaffected by the inclusion of the functional additives.

d. Faeces Quality Results

TABLE 5

Faeces quality data.

| PRODUCT | DT1245 | DT1246 | DT1247 | DT1248 | DT1249 | DT1250 |
|---|---|---|---|---|---|---|
| % SBP Inclusion | 0 | 0.8 | 1.7 | 2.5 | 3.3 | 4.1 |
| Mean Score | 5.2a | 5.9b | 6.0b | 5.9b | 6.0b | 5.8b |
| % Ideal Faeces | 26.2 | 36.6 | 47.1 | 45 | 42.2 | 39.4 |
| % Unacceptable Faeces | 18 | 5.6 | 2.9 | 3.8 | 3.9 | 9.2 |
| No. Defaecations | 61 | 71 | 70 | 80 | 102 | 109 |

Different letters in the same row denote significant difference (ANOVA $p < 0.05$). The control product (no SBP addition) gave significantly poorer mean faeces score than the other five diets. (ANOVA $p < 0.05$). Between the diets containing the various levels of SBP addition, there was no overall significant difference in mean faeces score. The percentage of ideal faeces shows a pattern of increasing and then decreasing levels with increasing levels of SBP addition. The percentage of unacceptable faeces shows the converse pattern.

Product DT1247, total SBP inclusion of 1.7%, total fibre content of 1.2%, produced the highest amount of ideal faeces (47.1%), and the lowest amount of unacceptable faeces (2.9%).

e. Faeces Quantity

The wet faeces output and the number of defecations given by the diets is shown below in table 6.

TABLE 6

| | Wet faeces output. | | | | | |
|---|---|---|---|---|---|---|
| PRODUCT | DT1245 | DT1246 | DT1247 | DT1248 | DT1249 | DT1250 |
| % SBP Inclusion | 0 | 0.8 | 1.7 | 2.5 | 3.3 | 4.1 |
| Wet faeces output gm/ 1000 kcal DE eaten | 124.1a | 153.2ab | 175.2bc | 185.0c | 245.9d | 303.7e |
| No. Defaecations | 61 | 71 | 70 | 80 | 102 | 109 |

Different letters in the same row denote significant difference (ANOVA p It 0.05). No. of defaecations given is the amount for six dogs over 7 days.

Wet faeces output decreased as the fibre inclusion level increased. At an inclusion level of 1.7% and above of SBP, the increase in wet faeces output was significantly greater than for the standard product.

The total number of defaecations increased as the amount of fibre in the diet increased, from 61 defaecations (per 6 dogs over 7 days, average 1.5 defaecations per dog per day) for the standard diet to 109 (per 6 dogs over 7 days, average 2.6 defaecations per dog per day) for the highest level of fibre addition.

f. Apparent Digestibilities

The standard product (DT1245, 0% SBP) gave good apparent digestibilities for all the major nutrients tested. The apparent digestibilities of all the nutrients showed a pattern of decreasing apparent digestibility as the level of SBP inclusion increased (see table 7). The apparent digestibility of fat given from the diets, fits the above pattern with the exception of the result from DT1246 (0.8% SBP inclusion). This result is slightly lower than would be expected.

TABLE 7

| | Apparent digestibilities. | | | | | |
|---|---|---|---|---|---|---|
| PRODUCT | DT1245 | DT1246 | DT1247 | DT1248 | DT1249 | DT1250 |
| % SBP Inclusion | 0 | 0.8 | 1.7 | 2.5 | 3.3 | 4.1 |
| Dry Matter | 80.1a | 77.9ab | 76.0b | 75.6bc | 72.8c | 69.3d |
| Organic Matter | 86.3a | 84.4ab | 83.2b | 82.4b | 78.7c | 75.2d |
| Protein | 85.8a | 85.5a | 83.7a | 83.3a | 82.5ab | 79.6b |
| Fat | 93.2a | 90.5bc | 92.2ab | 91.9abc | 90.6bc | 89.6c |
| Carbohydrate | 78.6a | 75.6ab | 75.1ab | 71.4b | 64.8c | 61.3c |
| Energy | 87.6a | 85.4ab | 84.2b | 84.0b | 80.6c | 77.3d |

All digestibilities are apparent percentages. Different figures in the same row denote significant difference (ANOVA p It 0.05). With the exception of dry matter and carbohydrate apparent digestibility, at the two highest inclusion level of SBP (DT1250 and DT1249) and carbohydrate apparent digestibility at the third highest inclusion level (DT1248), the other nutrients tested, in all products, all gave apparent digestibilities of greater than 75%.

The levels of SBP inclusion at which the apparent digestibilities become significantly lower than the standard (0% SBP inclusion) are as follows:

| Dry matter: | 1.7% SBP (1.2% fibre content) |
|---|---|
| Organic matter: | 1.7% SBP (1.2% fibre content) |
| Protein: | 4.1% SBP (3.2% fibre content) |
| Fat: | 3.3% SBP (2.5% fibre content) |
| | (assuming the result from 0.8% SBP is an anomaly) |
| Carbohydrate: | 2.5% SBP (1.6% fibre content) |
| Energy: | 1.7% SBP (1.2% fibre content) |

DISCUSSION

The effect of the addition of SBP to canned products is clear for all the parameters measured. In terms of faeces quality, the performance of the control was poorer than expected. Nevertheless, the effect of SBP is clear and the addition of SBP, at all of the levels tested, gave a significant improvement in faeces quality.

In these trials, the optimum level of SBP addition was 1.7%, giving a total fibre content of the diet of 1.2% as is. However, whilst the 1.7% inclusion level produced the greatest percentage of ideal and the least percentage of unacceptable faeces, this inclusion level did not give significantly better overall faeces quality than any of the other inclusion levels.

The addition of the SBP increased the number of times the dogs defecated. This can be explained by increased volume of faeces produced by the higher fibre diets. The increase in the indigestible ingredient in the recipe, as would be expected, increased the volume of faeces produced. With an inclusion level of SBP of 1.7%, (the inclusion level that gave the best faeces quality) the wet faeces output was 175.2 gm/1000 kcal DE eaten. At the level of SBP inclusion that gave optimal faeces quality ie 1.7% (DT1247), the apparent digestibilities were all good.

CONCLUSION

To improve faeces quality, any level of SBP inclusion (of 0.8% or more) produces a significant improvement compared to the standard (no SBP) product. The best faeces quality was produced at an inclusion level of 1.7%. However, an inclusion level of 0.8% also gave a significant improvement in faeces quality, without a significant increase in wet faeces output. Above this level, in this trial, the faeces output was significantly increased. These results therefore provide us with the ability to adjust fibre content in line with the desired product performance.

The palatability of the final product was not adversely affected by SBP nor slippery elm meal inclusion as compared with the standard.

3. Pet Food Products Aiming to Improve Pet Animal Natural Defenses

The following examples are directed to the aspect of the invention concerned with improving the immune function of pet animals by daily feeding of a food which incorporates prescribed levels of functional antioxidant ingredients.

Typical diets were based on standard dry kibble dog food products, with prescribed levels of antioxidants added. Control diets were also manufactured and fed.

The objective of testing was to demonstrate an increase in antioxidant status in dogs fed the test diets, as compared to those fed the control diets. Antioxidant level gives an indication as to the status of the immune system of the pet. The test was also conducted to determine suitable levels of functional ingredients for incorporation in a treat product to be fed on a daily basis, without adverse effects on the product's palatbility.

The specification for antioxidant levels to be incorporated into the diet is:

| Ingredient | Active Compounds | Final Level in Prod |
|---|---|---|
| Taurine | Taurine | 200 mg/400 kcal |
| Vitamin B complex | Vitamin B | 0.2% by mass |
| Marigold Meal | Lutein | 0.5 mg Lutein/400 kcal |
| Alpha-Tocopherol Acetate | Vitamin E | 50 IU/400 kcal |
| Vitamin C | Vitamin C | 40 mg/400 kcal |

The test diet was fed to a panel of 12 dogs of mixed breeds, age and sex. The control diet has been fed to a panel of 6 dogs of mixed breeds, age and sex.

Both these diets have been analysed; the results are as follows:

| Ingredient/Antioxidant | Test Diet JH017 | Control Diet JH016 |
|---|---|---|
| Protein % | 27.6 | 27.2 |
| Fat % | 13 | 12.7 |
| Moisture % | 5.8 | 7.1 |
| Ash % | 7.6 | 7.2 |
| Energy Density (PME) | 368 kcal/100 g | 364 kcal/100 g |
| Vitamin E | 52 IU/400 kcal | 17 IU/400 kcal |
| Vitamin C | 2.5% | 0.25% |
| Taurine | 0.27% | 0.08% |
| Vitamin B complex | 0.2% | 0.02% |

++The test diet included small amounts of tomato powder and lucerne.

Bleeds to measure plasma absorption of vitamins E and C, taurine and carotenoids were conducted at weeks 0, 4 and 6. The results are illustrated in FIG. 3.

Differences in Plasma vit E Status Between Test and Control Groups After 6 Weeks of Feeding.

Figure 1:
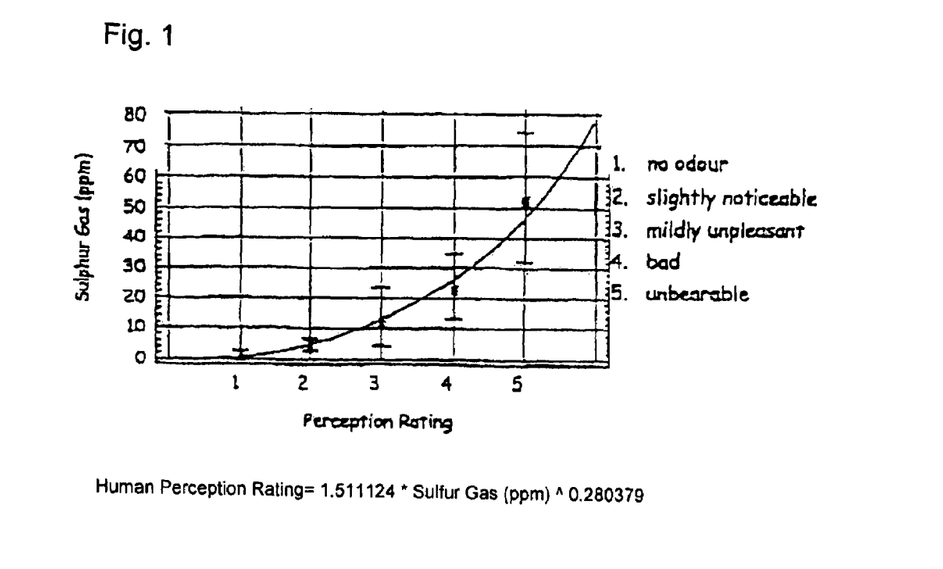
FIG. 1 Graph illustrating a human perception analysis identifying the human detection limits of flatulence episodes.
Figure 2:
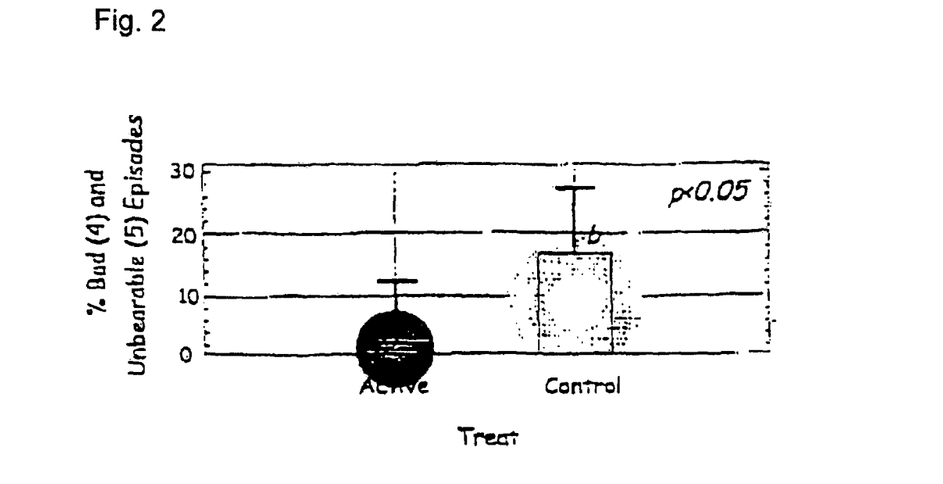
FIG. 2 Graph illustrating the mean percentage of combined bad and unbearable episodes produced when dogs were few active and control treats.
Figure 3:
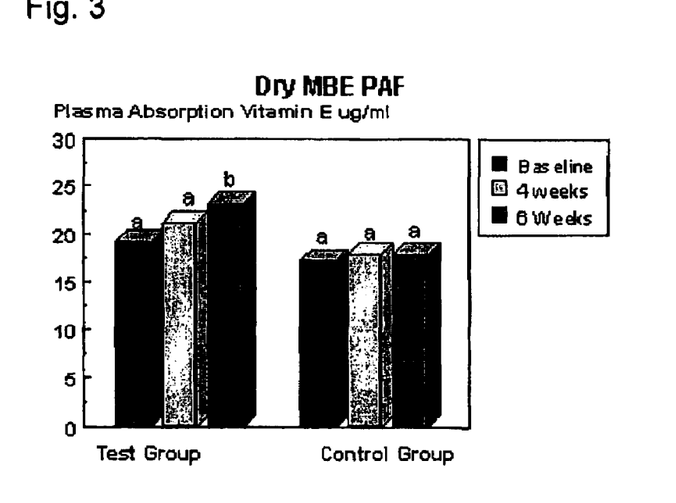
FIG. 3 Graph illustrating the difference in plasma vitamin E status between test and control groups after 6 weeks of feeding.

FIG. 3 graph illustrates a distinct and statistically significant rise (paired T-test, p It 0.05) by 19.6% in plasma vitamin E status in the test group after 6 weeks of feeding. This has not been observed in the control group.

Figure 4A:
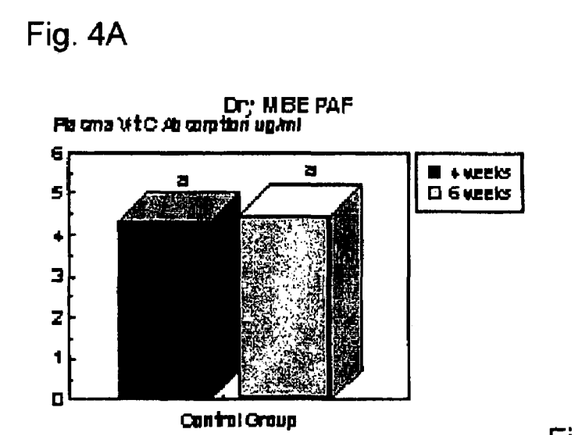
FIGS. 4A, 4B Graphs illustrating the difference in plasma vitamin C status between test and control groups after 6 weeks of feeding.
Figure 4B:
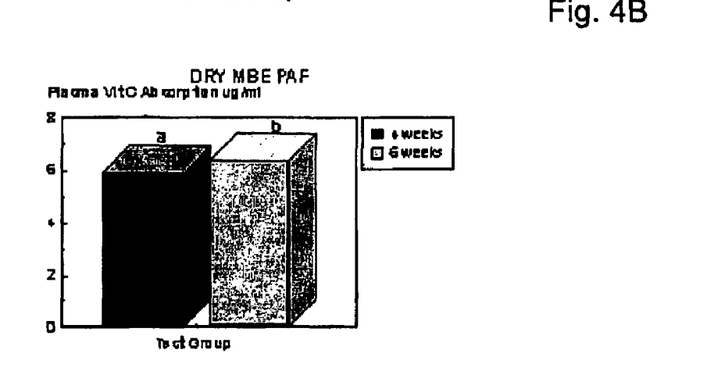

Plasma Absorption of Vitamin C:

FIGS. 4A and 4B. Differences in Plasma vit C Status Between Test and Control Groups After 6 Weeks of Feeding.

Baseline plasma vitamin C level results for dogs in the test and control groups were unreliable and therefore have not been included in the data set. Using a paired T-test, a statistically significant difference (p It 0.05) is achieved when comparing the plasma vitamin C level of the test and control group at 6 weeks.

Figure 5:
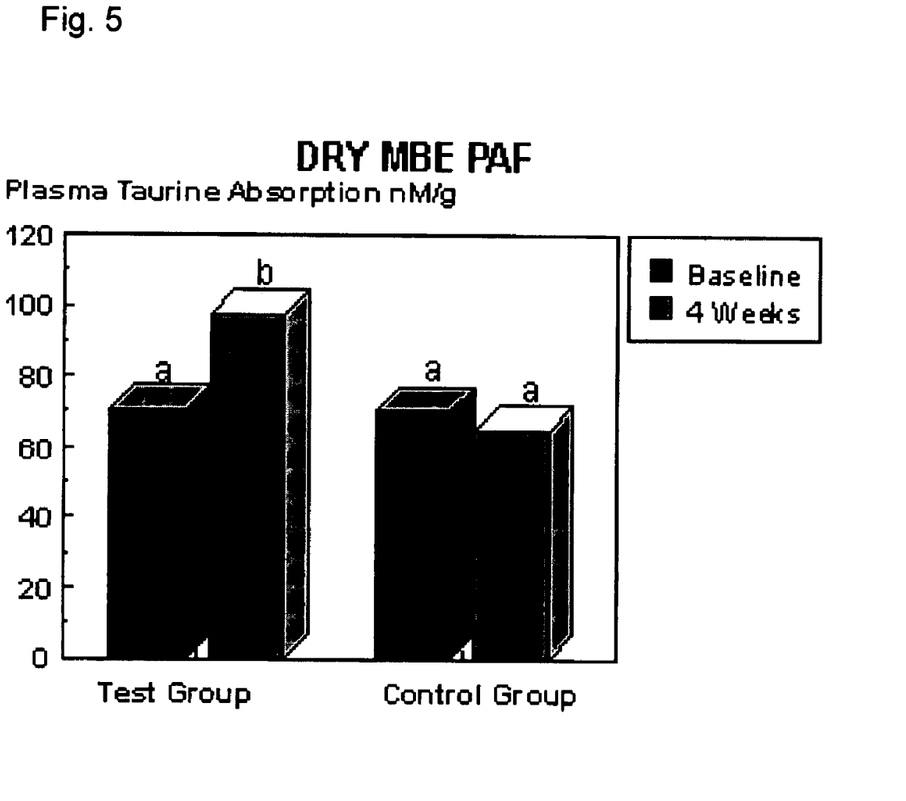
FIG. 5 Graph illustrating the difference in plasma taurine status between test and control groups after 4 weeks of feeding.

Plasma Absorption of Taurine:

FIG. 5. Differences in Plasma Taurine Status Between Test and Control Groups After 4 Weeks of Feeding.

This graph illustrates a distinct and statistically significant rise (paired T-test, p It 0.05) by 38% in plasma taurine status in the test group after 4 weeks of feeding. This has not been observed in the control group.

The test results indicate that feeding a treat, fortified with an additional antioxidant blend of the type, and at the same daily dosage level, used in this trial, increases the levels of vitamins E and C and taurine in the animal. It was also noted that the palatability of the food was not adversely affected by the inclusion of the functional ingredient blend 4. Pet Foods Products Aimed at Reducing Signs of Stress The following examples are directed to the aspect of the invention concerned with achieving reduction in stress-related indicators of animal behaviour by daily feeding of a supplementary treat, in conjunction with its normal feeding regime.

SUMMARY

This example details the observed effect on dogs which have been fed a meaty 'treat'-style chewable tablet, containing a formulation of plant extracts, on a daily basis.

In a veterinary supervised trial, 27 adult dogs (free living dogs of mixed breed, age and sex) having been identified as exhibiting signs or behaviour indicative of mild stress, anxiety or nervousness, consumed the test product daily over a period of at least four weeks.

Of the trial dogs, 25 were observed to have reduced one or more signs of: nervousness (19), nervous dermatitis (9), attention seeking syndrome (4), travel upset (4), mild separational anxiety (2), "show nerves" (3). Two dogs failed to show any change to signs of their nervous or anxiety state.

It is therefore concluded that the preparation when consumed daily, according to the directions given in Table 1, will have a high likelihood of providing a reduction in signs of mild stress, anxiety and nervousness in adult dogs. It is also concluded that the presence of the functional ingredients in the test product did not adversely affect the palatability of the product.

| Animal Mass | Daily Dosage |
|---|---|
| <7 kg | 2.5 g |
| 7-14 kg | 5.0 g |
| 15-25 kg | 10 g |
| >25 kg | 20 g |

The formulation of the test product was as follows:

A meaty based chew (10 g) containing:

| Ingredient | % by mass |
|---|---|
| Ground or pulverised meat | 50 |
| Cereal | 11 |
| Sugar | 7.8 |
| Preservatives | 9.7 |
| Antioxidant | 0.1 |
| Gelatine | 3.8 |
| Potassium sorbate | 0.4 |
| Water | 10.5 |
| Magnesium sulfate | 1.8 |
| Kava root extract | 2.0 |
| Valerian root extract | 0.40 |
| Vitamin B | 2.5 |

In summary, it has been demonstrated that it is possible, in accordance with the different above described aspects of the invention, to formulate treat-style pet food products having a combination of specific functional additives that achieve an improvement of specified health indicators, without adversely affecting the palatability of the food product.

The invention claimed is:

1. A packaged treat-sized pet food product comprising:
   a manufactured food substrate; and
   a combination of non-palatable, functional additives incorporated in the food substrate, including from 6 to 14% by weight of the finished product of vegetable charcoal, from 0.3 to 0.8% by weight of the finished product of salts of zinc and from 0.05 to 0.11% by weight of the finished product of Yucca Shidigera or Elata extract, wherein said functional additives are present in amounts sufficient to reduce flatulence odour when the pet food product is provided to a pet animal on a regular daily basis, and wherein said food substrate is present in a proportion sufficient to mask the flavor and/or odor of the non-palatable additives.

2. The packaged pet food product according to claim 1, wherein the salts of zinc comprise zinc acetate, and wherein the functional additives are provided in the following amounts, by weight of finished product, the balance being made-up by the manufactured food substrate and other nutritional supplements:
   0.06% Yucca Shidigera or Elata extract;
   6% Vegetable charcoal; and
   0.4% zinc acetate.

3. The packaged pet food product according to claim 1, wherein the food substrate includes dry ingredients comprising animal protein, carbohydrates and an anti-microbial agent, and at least one liquid ingredient in a predetermined ratio to the sum of the dry ingredients.

4. The packaged pet food product according to claim 2, wherein the food substrate includes dry ingredients comprising animal protein, carbohydrates and an anti-microbial agent, and at least one liquid ingredient in a predetermined ratio to the sum of the dry ingredients.

5. The packaged pet food product according to claim 3, wherein the animal protein constitutes from about 17% to 50% by weight of the dry ingredients.

6. The packaged pet food product according to claim 5, wherein the animal protein is derived from beef, pork, mutton, poultry, fish or a combination of these.

7. The packaged pet food product according to claim 6, wherein the animal protein includes gelatins.

8. The packaged pet food product according to claim 3, wherein the carbohydrates include simple and complex carbohydrates wherein the complex carbohydrates include rice flour, and wherein the simple carbohydrates include glucose, glycerol and/or sugar.

9. The packaged pet food product claim 3, wherein the antioxidant is rosemary extract.

10. The packaged pet food product according to claim 3, wherein the water constitutes about 10 to about 20% by weight of the finished product.

11. The packaged pet food product in accordance with claim 5, wherein the pet food product is in the form of a palatable, 'treat'-sized, chewy tablet, including the following ingredients in proportions by weight of the finished product:
   gelatine—from about 3 to about 7%;
   glucose—from about 2 to about 5%;
   sugar—from about 2 to about 5%;
   glycerol—from about 1 to about 4%;
   potassium sorbate—from about 0.2 to about 0.5%;
   rosemary extract—from about 0.01 to about 0.05%,
   water—from about 10 to about 20%; and
   the balance being composed of pulverised meat (approx 50%), cereal flour (approx 11%), sugar (approx 8%), glycerine (approx 9%), citric acid (approx 1%) and preservatives (approx 0.1%).

12. The packaged pet food product according to claim 11, wherein the product is provided in the form of a biscuit or multi-piece biscuit that is easily divisible so as to facilitate administration to a pet animal of a desired amount of the product corresponding with a desired dosage of the functional additives.

13. The packaged pet food product according to claim 11, wherein the product is provided in the form of a food bar, having substantially uniform concentration of the functional additives throughout the length thereof, and wherein the food bar includes markings, etchings or the like for indicating where the food bar may be broken so as to provide the pet animal with a desired dosage of the functional additives.

14. A process for manufacturing a palatable, treat-sized pet food product comprising a manufactured food substrate and a combination of non-palatable, functional additives incorporated in the food substrate, including from 6 to 14% by weight of the finished product of vegetable charcoal, from 0.3 to 0.8% by weight of finished product of salts of zinc and from 0.05 to 0.11% by weight of the finished product of Yucca Shidigera or Elata extract, wherein the functional additives include two or more additives selected from the group consisting of Yucca extract, vegetable charcoal and salts of zinc, and wherein said food substrate is present in a proportion sufficient to mask the flavor and/or odor of the non-palatable additives, comprising the steps of:
   mixing dry ingredients including animal protein, carbohydrates and an antimicrobial agent;
   heating the dry ingredient mixture to between 50 to 80° C., preferably about 60° C., for about 5 to 15 minutes, preferably about 10 minutes;
   adding the functional additives to the dry ingredient mixture, wherein the functional additives are present in amounts sufficient to reduce flatulence odour when the pet food product is provided to a pet animal on a regular, preferably daily basis;
   mixing the resultant mixture for about 5 minutes;
   heating, in a separate container liquid ingredients, including water and an antioxidant, to between 60 to 85° C., preferably about 75° C.; adding the heated liquid ingredients to the resultant mixture to obtain a moistened mixture; heating the moistened mixture to between 60 to 80° C., preferably about 75° C., for about 5 minutes to obtain a processed mixture;
   substantially immediately after the heating step subjecting the processed mixture to a cooling step to achieve product temperature of between 40 to 60° C.; and
   moulding the cooled mixture by impression moulding or cutting techniques so as to form a packagable product of predetermined size, shape and weight.

15. The process of claim 14, further including the step of making markings, etchings or the like on the packagable product so as to enable the product in use, to be easily broken into pieces of a particular size.

16. The process of claim 14, wherein the processed mixture is subject to a cooling step to achieve product temperature of about 50° C.

17. The process of claim 14, wherein the salts and zinc comprise zinc acetate, and wherein the functional additives are provided in the following amounts, by weight of finished product, the balance being made-up by the manufactured food substrate and other nutritional supplements:
   0.06% Yucca Shidigera or Elata extract;
   6% Vegetable charcoal; and
   0.4% zinc acetate.

* * * * *